United States Patent
Kuwabara

(10) Patent No.: US 9,050,059 B2
(45) Date of Patent: Jun. 9, 2015

(54) RADIATION IMAGING APPARATUS AND SYSTEM

(71) Applicant: FUJIFILM CORPORATION, Tokyo (JP)

(72) Inventor: Takeshi Kuwabara, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 247 days.

(21) Appl. No.: 13/736,826

(22) Filed: Jan. 8, 2013

(65) Prior Publication Data
US 2013/0182823 A1 Jul. 18, 2013

(30) Foreign Application Priority Data
Jan. 12, 2012 (JP) .................................. 2012-003800

(51) Int. Cl.
*G01N 23/02* (2006.01)
*A61B 6/00* (2006.01)

(52) U.S. Cl.
CPC ............... *A61B 6/542* (2013.01); *A61B 6/4233* (2013.01); *A61B 6/4283* (2013.01); *A61B 6/467* (2013.01)

(58) Field of Classification Search
USPC ............... 378/28, 29, 37, 162, 163, 164, 165, 378/166, 189, 190
See application file for complete search history.

(56) References Cited

U.S. PATENT DOCUMENTS

| | | | |
|---|---|---|---|
| 6,516,098 B2 | 2/2003 | Nonaka | |
| 6,643,411 B2 | 11/2003 | Nonaka | |
| 6,999,121 B2 | 2/2006 | Endo | |
| 7,436,444 B2 | 10/2008 | Endo | |
| 2012/0082294 A1* | 4/2012 | Virshup et al. | 378/62 |
| 2013/0126742 A1* | 5/2013 | Hayun et al. | 250/366 |

FOREIGN PATENT DOCUMENTS

| | | |
|---|---|---|
| JP | 11-151233 A | 6/1999 |
| JP | 2002-181942 A | 6/2002 |
| JP | 2006-122667 A | 5/2006 |
| JP | 2008-108440 A | 5/2008 |
| JP | 2011-185622 A | 9/2011 |

OTHER PUBLICATIONS

Notification of Reason(s) for Refusal dated Dec. 25, 2013, with English translation.

* cited by examiner

*Primary Examiner* — Nicole Ippolito
(74) *Attorney, Agent, or Firm* — McGinn IP Law Group, PLLC

(57) ABSTRACT

An X-ray imaging apparatus has an electronic cassette, in which an FPD device receives X-rays applied by an X-ray source to a body, and stores charge according to a radiation dose of the X-rays, to create an image. A control unit controls the FPD device. A radiation sensor detects the radiation dose to be used for controlling the FPD device. A magnet as fastening device secures the radiation sensor removably in a radiation path between the X-ray source and the body. Also, an evaluation unit recognizes a start and end of application of the X-rays according to a dose signal from the radiation sensor, for the control unit to control the FPD device. A flexible support arm is disposed between the radiation sensor and the magnet, for keeping the radiation sensor in a changeable position relative to the magnet.

20 Claims, 10 Drawing Sheets

RADIATION IMAGING APPARATUS AND SYSTEM

BACKGROUND OF THE INVENTION

1. Field of the Invention

The present invention relates to a radiation imaging apparatus and system. More particularly, the present invention relates to a radiation imaging apparatus and system in which the start and end of irradiation is recognized according to a detected radiation dose, and in which reliability of the recognition of the start and end of the irradiation can be high.

2. Description Related to the Prior Art

A radiation imaging system is well-known medical system for use with X-rays as radiation. The radiation imaging system includes an X-ray generation apparatus and an X-ray imaging apparatus for creating an X-ray image by receiving X-rays from a body (object) of a patient. The X-ray imaging apparatus includes a radiation source, a controllable power supply (source control unit), and a radiation switch. The controllable power supply drives the radiation source. The radiation switch is operable for inputting a signal for starting the irradiation. The X-ray imaging apparatus includes a radiation detector and a console unit. The radiation detector detects the X-rays from the body to create the X-ray image. The console unit controls the radiation detector and also displays the X-ray image.

In a recent type of the radiation detector in the radiation imaging system, an FPD device (flat panel detector device) or detector panel is incorporated instead of an X-ray film or imaging plate (IP). The FPD device includes numerous arrays of pixels for storing signal charge according to dose of X-rays. The signal charge is stored by each of pixels in the FPD device, and converted into a voltage signal by a signal processing unit, to detect the X-ray image of information of an object image. Image data of a digital form of the X-ray image is output.

As a portable type of the radiation detector, an electronic cassette as a radiation detecting cassette is known, and includes a quadrilateral housing and the FPD device contained in the housing. The electronic cassette is removably mounted on a floor stand or frame support for examination in an upright position. The floor stand is a well-known device commonly used with any one of a film cassette, IP cassette and various units. In contrast with an installed type of detector, the electronic cassette is also placed on a bed, or held manually by a patient for imaging a body part which could not be imaged easily with the installed type. Also, the electronic cassette is transported out of a hospital for the purpose of emergency medicine for a patient of an accident or disaster, or diagnosis of a home-care patient.

In the FPD device, resetting is carried out to discharge dark current or unwanted charge of pixels of images of earlier imaging in order to minimize influence of noise to the X-ray image. In the radiation detector with the FPD device in general, it is necessary to synchronize a start of the irradiation with an end of the resetting to start the storing. To this end, a communication interface is disposed between the controllable power supply and the radiation detector. A start signal is generated by the controllable power supply for the irradiation, and transmitted input to the radiation detector. The storing of the radiation detector is triggered by receiving the start signal.

Also, an AEC (or automatic exposure control) is carried out in the radiation detector. A radiation sensor or dosimeter is associated with the radiation detector, and detects a radiation dose of X-rays passed through the body. When an accumulated value of the radiation dose from the radiation sensor increases and becomes equal to a predetermined threshold, the irradiation of the X-ray imaging apparatus is stopped, to change over the radiation detector from the storing to the reading.

It is likely that no communication interface is present with the controllable power supply. In one type of the radiation detector, a start and end of the irradiation are recognized according to a comparison of the radiation dose with a threshold. The radiation detector starts the storing if the start is recognized. The radiation detector changes over from the storing to the reading if an end of the irradiation is recognized.

In U.S. Pat. Nos. 6,516,098 and 6,643,411 (corresponding to JP-A 11-151233), the radiation sensor is disposed behind the FPD device directed to the body. The start and end of the irradiation is recognized according to an output of the radiation sensor. According to the document, a separate structure of the radiation sensor from the FPD device is suggested. Also, disposition of the radiation sensor is not limited to the backside of the FPD device.

U.S. Pat. Nos. 6,999,121 and 7,436,444 (corresponding to JP-A 2002-181942) discloses a type of the X-ray imaging apparatus in which the radiation sensor is disposed inside a housing or chassis for containing the FPD device. JP-A 2011-185622 discloses the X-ray imaging apparatus in which a bias voltage is applied to pixels of the FPD device and the radiation dose is detected by monitoring a current flowing in a bias line for supplying a bias voltage. The bias line and a current meter for measuring the current in the bias line are combined to correspond to the radiation sensor.

Various problems may occur upon delay of the start and end of the irradiation. If the recognition of the start delays, part of the charge according to X-rays applied before the recognition is not stored in pixels. Degradation of the X-ray image occurs. Also, the body of the patient is likely to receive unwanted radiation. It is necessary to recognize the start and end of the irradiation quickly. For example, time of the irradiation for imaging the chest is as short as 50 msec. The start and end of the irradiation must be recognized in a very short time.

To detect the radiation dose of X-rays passed through the body as described in the above documents is influenced by attenuation of the X-rays after the passage. There occurs a problem in the irradiation at a relatively low dose of the radiation dose. The detection of the start and end of the irradiation may be delayed. Also, failure in the detection of the start and end of the irradiation may occur.

In the above documents, the radiation sensor is stationary and does not have freedom in the disposition. Influence of the attenuation to the imaging occurs in the presence of the body. Although it is disclosed in U.S. Pat. Nos. 6,516,098 and 6,643,411 that the disposition of the radiation sensor is not limited, the position of the radiation sensor may be modified as desired by a user for attachment. The radiation sensor cannot be moved form the set position once the radiation sensor is positioned. There is no suggestion of degree of freedom in positioning the radiation sensor.

SUMMARY OF THE INVENTION

In view of the foregoing problems, an object of the present invention is to provide a radiation imaging apparatus and system in which the start and end of irradiation is recognized according to a detected radiation dose, and in which reliability of the recognition of the start and end of the irradiation can be high.

In order to achieve the above and other objects and advantages of this invention, a radiation imaging apparatus includes a radiation detector, having a detector panel, for receiving radiation applied by a radiation source to an object, and storing charge according to a radiation dose of the radiation, to create an image. A first radiation sensor detects the radiation dose. An evaluation unit recognizes a start and/or end of application of the radiation according to a dose signal from the first radiation sensor. A control unit controls the detector panel according to an evaluation result of the evaluation unit. A fastening device secures the first radiation sensor removably in a radiation path between the radiation source and the object.

Furthermore, a flexible support arm, disposed between the first radiation sensor and the fastening device, for keeping the first radiation sensor in a changeable position relative to the fastening device.

The fastening device includes a magnet device.

In another preferred embodiment, the fastening device includes a clip device.

In one preferred embodiment, the fastening device is formed together with the first radiation sensor.

Furthermore, a radio transmitter/receiver transmits the dose signal from the first radiation sensor to the evaluation unit.

In still another preferred embodiment, furthermore, a signal line transmits the dose signal from the first radiation sensor to the evaluation unit.

The first radiation sensor is disposed near to an exit aperture of the radiation source for emitting the radiation.

In one preferred embodiment, the first radiation sensor is disposed in an area where the radiation leaks from the radiation path inside the radiation source.

In another preferred embodiment, the support arm extends toward the radiation source from a side of the radiation detector opposed to the object, and allows the first radiation sensor at an arm end thereof to enter the radiation path between the radiation source and the object.

The fastening device is disposed on the radiation detector. Furthermore, a support arm is disposed to extend in a radiation direction of the radiation, having first and second end portions, the first end portion having the fastening device, the second end portion supporting the first radiation sensor.

The first radiation sensor is disposed behind the object to which the radiation detector is directed.

In one preferred embodiment, the control unit and the evaluation unit are incorporated in the radiation detector.

The evaluation unit is external to the radiation detector, and transmits the evaluation result wirelessly or by a wired connection.

In still another preferred embodiment, furthermore, a second radiation sensor is disposed on the detector panel, for detecting the radiation dose discretely from the first radiation sensor.

The control unit compares the radiation dose with a reference dose conditioned previously, and selects one of outputs of the first and second radiation sensors for use according to a result of comparison of the radiation dose.

The second radiation sensor is used for automatic exposure control.

The second radiation sensor is part of the pixels of the detector panel.

In one preferred embodiment, furthermore, a communication interface is connected with the evaluation unit, for receiving the dose signal from the first radiation sensor, and transmitting the evaluation result to the control unit.

The radiation detector includes a portable housing for containing the detector panel.

Also, a radiation imaging system is provided, and includes a radiation source for applying radiation to an object. A radiation detector has a detector panel, for receiving the radiation applied to the object, and storing charge according to a radiation dose of the radiation, to create an image. A control unit controls the detector panel. A first radiation sensor detects the radiation dose to be used for controlling the detector panel. A fastening device secures the first radiation sensor removably in a radiation path between the radiation source and the object.

Furthermore, a mobile housing contains at least the radiation source, the mobile housing being mobile for a bedside use.

Accordingly, reliability of the recognition of the start and end of the irradiation can be high, because the fastening device can position the radiation sensor suitably for the radiation.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
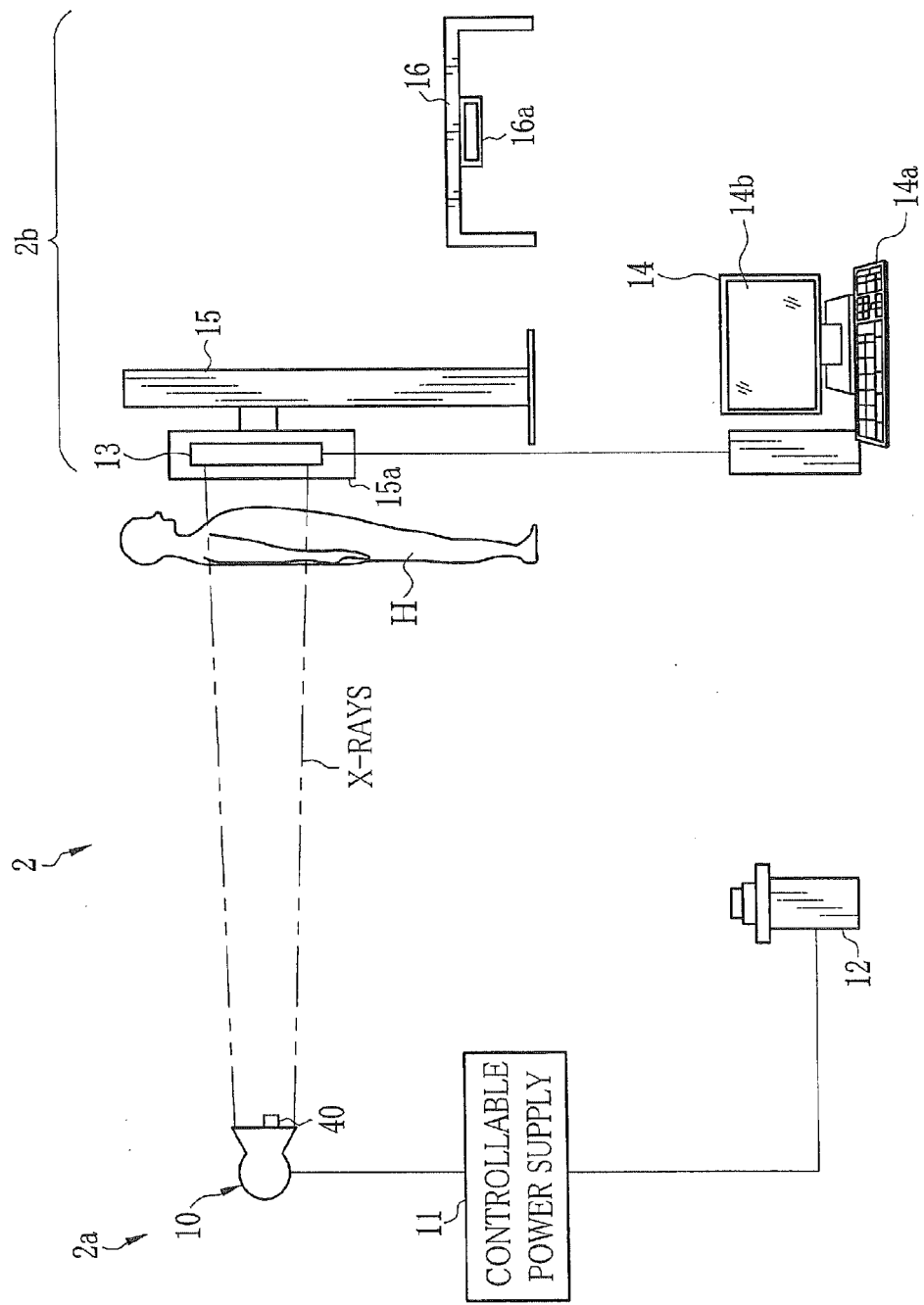
FIG. 1 is an explanatory view in elevation illustrating an X-ray imaging system.

In FIG. 1, an X-ray imaging system 2 as radiation imaging system includes an X-ray source 10 as radiation source, a controllable power supply 11 (source control unit), a radiation switch 12, an electronic cassette 13 as a radiation detector or radiation detecting cassette, a console unit 14, a floor stand 15 or frame support for examination in an upright position, and an examination table 16 for a supine position. The controllable power supply 11 drives the X-ray source 10. The radiation switch 12 is operable for starting irradiation of X-rays. The electronic cassette 13 detects X-rays transmitted through a body H (object) of a patient and outputs an X-ray image. The console unit 14 is a user interface for controlling the electronic cassette 13 and displaying the X-ray image. Among those, an X-ray generation apparatus 2a as radiation generation apparatus is constituted by the X-ray source 10, the controllable power supply 11 and the radiation switch 12. An X-ray imaging apparatus 2b as radiation imaging apparatus is constituted by the electronic cassette 13 and the console unit 14. Also, a moving device (not shown) is installed for moving the X-ray source 10 in a direction and to a position as required for the purpose.

Figure 5:
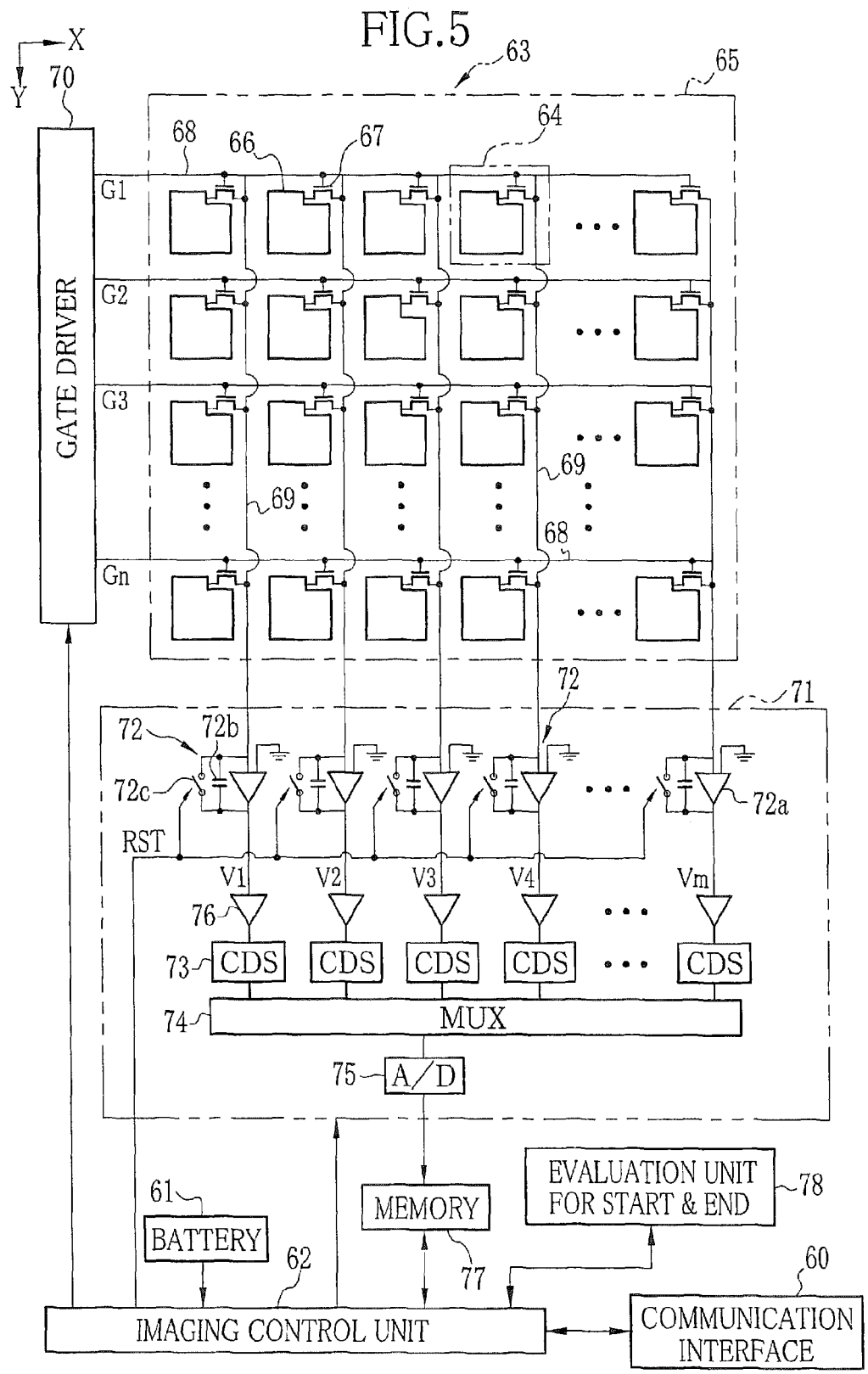
FIG. 5 is a block diagram schematically illustrating circuit elements in an electronic cassette.

The electronic cassette 13 includes an FPD device 63 (flat panel detector device) or detector panel of FIG. 5 and a portable housing (not shown) for containing the FPD device 63. The housing is in a shape of a rectangular quadrilateral, extends flatly and has a horizontal size substantially the same as that of a film cassette and IP cassette (CR cassette) according to the International Standards ISO 4090:2001. The electronic cassette 13 can be mounted also on a mount or an examination table of a type for the film cassette or IP cassette as well-known in the art.

Two or more electronic cassettes 13 are prepared per one examination room where the X-ray imaging system 2 is installed, for example, one for the floor stand 15 and one for the examination table 16. Holders 15a and 16a of the floor stand 15 and the examination table 16 receive the electronic cassette 13 in a removable manner so that an imaging surface 65 of the FPD device 63 (See FIG. 5) is positioned in a radiation path from the X-ray source 10. In addition to the use of the floor stand 15 and the examination table 16, the electronic cassette 13 can be used solely, for example, can be placed on a bed or table where the body H lies, or held manually by hands of the body H.

The console unit 14 is on-line with the electronic cassette 13 for communication by a wired connection or wirelessly. When an input interface 14a such as a keyboard is operated by an operator, a control signal is entered to the console unit 14 to control the electronic cassette 13. Specifically, the console unit 14 turns on and off a power source of the electronic cassette 13, and changes over the electronic cassette 13 to a standby mode, imaging mode and the like.

A display panel 14b in the console unit 14 is driven to display an X-ray image from the electronic cassette 13. Data of the X-ray image is written to a data storage or memory in the console unit 14, an image server connected to the console unit 14 by the network, or other storage medium.

The console unit 14 receives inputs of personal information of the patient in relation to a diagnosis case, such as sex, age, body part, hospital department, purpose and the like, and causes the display panel 14b to display the information of the diagnosis case. The diagnosis case information is originally supplied by an outer system for managing patient information or diagnosis information, such as the HIS (Hospital Information System) and RIS (Radiography Information System). Also, the diagnosis case information can be input originally by an operator or technician manually. The diagnosis case information includes body parts, such as head, chest and abdomen, orientations of the body H, such as frontal, lateral and oblique orientations, and radiation directions including the posterior to anterior (P-A) direction for directing X-rays to the back of the body H, and the anterior to posterior (A-P) direction for directing X-rays to the front of the body H. He or she observes the diagnosis case information on the display panel 14b, and selectively determines an imaging condition by viewing images on the console unit 14.

The input interface 14a is operable in the console unit 14 for inputting information of an imaging condition for each of various body parts. The information of the imaging condition includes a tube voltage to determine energy spectrum of X-rays applied by the X-ray source 10, a tube current to determine dose of X-rays per unit time, and thresholds for a start and end of the irradiation for use in determining the start and end in comparing with a dose signal (dose information) generated by a first radiation sensor 40 or dosimeter. The information of the imaging condition is stored in a storage medium. When one of the body parts is designated by use of the input interface 14a, one of plural imaging conditions is read from the storage medium, and input to the electronic cassette 13.

Figure 2:
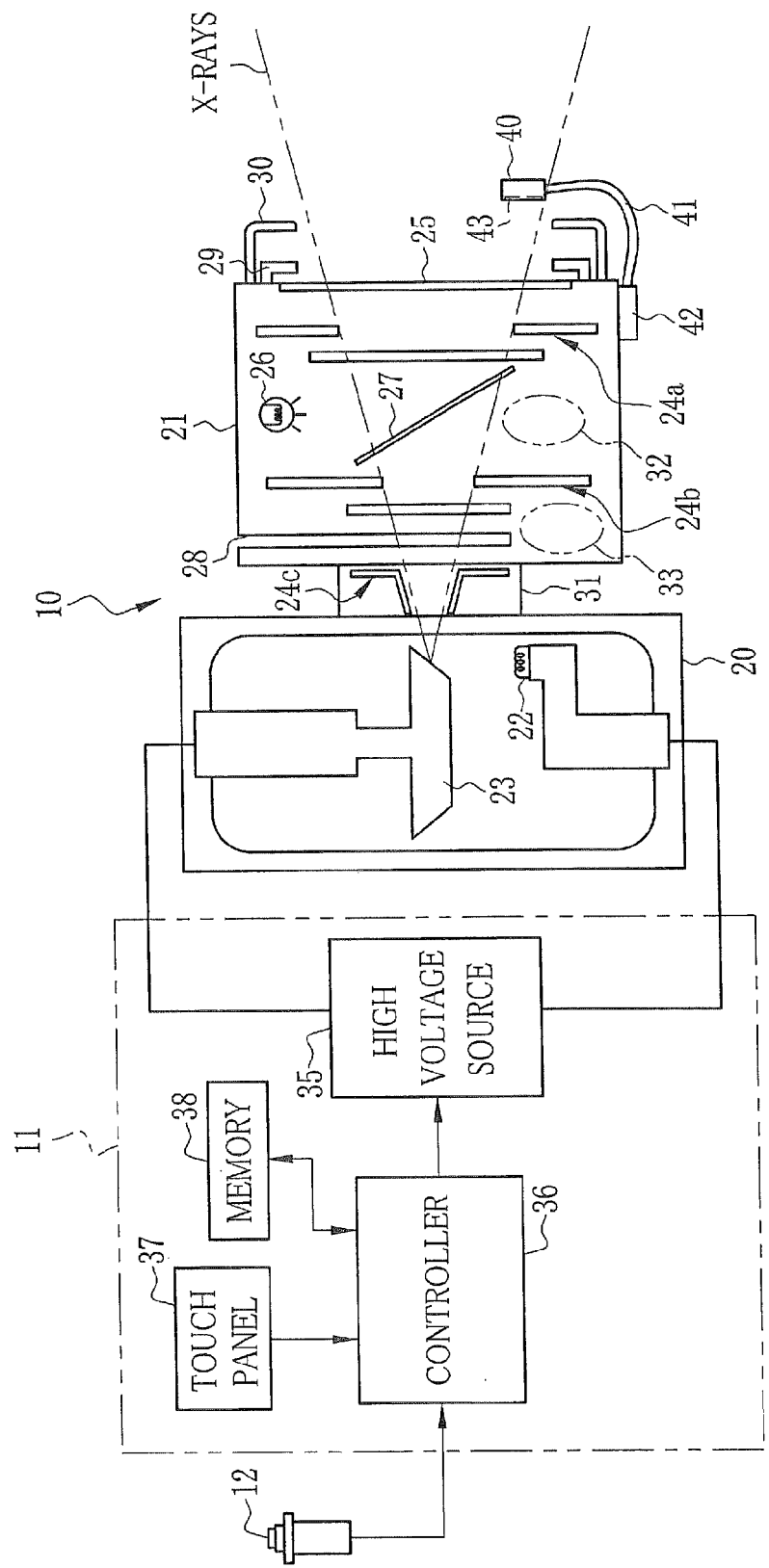
FIG. 2 is an explanatory view in elevation illustrating a radiation source, a controllable power supply and a radiation sensor.

In FIG. 2, the X-ray source 10 includes an X-ray tube 20 and a collimator 21 (aperture device) for limiting a radiation field of X-rays. The X-ray tube 20 includes a cathode 22 and an anode 23. The cathode 22 has filaments for emitting thermal electrons. The anode 23 as a target undergoes collision of the thermal electrons from the cathode 22, and emits X-rays.

The collimator 21 includes collimator plates 24a, 24b and 24c, which are plates of lead for shielding X-rays, are arranged in a frame form, and have center openings for passing X-rays. The collimator plates 24a-24c are shifted two-dimensionally to change the sizes of the center openings to limit the radiation field of X-rays. A radio transparent plate 25 is disposed in front of the collimator 21. An exit aperture of the collimator 21 is defined with the collimator plates 24a and the radio transparent plate 25. Also, the collimator 21 includes a halogen lamp 26, a mirror 27, a slot 28, a rail 29 and a front guard 30. The halogen lamp 26 illuminates for visually checking the radiation field of the collimator 21 after the adjustment. The mirror 27 reflects light from the halogen lamp 26 to the outside. The slot 28 and the rail 29 are used for setting an additional filter.

The controllable power supply 11 includes a high voltage source 35 and a controller 36. The high voltage source 35 has a transformer and a cable. The transformer boosts an input voltage to generate a high voltage. The cable is used to supply the anode 23 and the cathode 22 of the X-ray tube 20 with the high voltage. The controller 36 controls the high voltage, a tube current and an irradiation time of X-rays. The X-ray generation apparatus 2a does not have an interface on-line with the X-ray imaging apparatus 2b. A touch panel 37 of the controllable power supply 11 is manipulated by a technician or operator to input the high voltage, the tube current and the irradiation time of X-rays as an imaging condition. A memory 38 of the controllable power supply 11 stores a plurality of imaging conditions. The operator inputs the imaging condition by viewing an imaging condition set by the console unit 14.

The radiation switch 12 is a two-stage switch operable manually by an operator, and when depressed halfway as a first stage, generates a warmup signal for starting warmup of the X-ray source 10, and when depressed deeply as a second stage, generates a start signal for starting the X-ray source 10 to irradiate. Those signals are input to the controller 36 by a signal cable.

The controller 36 causes the high voltage source 35 to supply the X-ray source 10 with power upon receiving the start signal from the radiation switch 12. The controller 36 also actuates a timer to measure the irradiation time of X-rays. When the irradiation time elapses, the supply of power from the high voltage source 35 to the X-ray source 10 is stopped. The irradiation time is changeable according to the imaging condition or body part of target. For imaging of a still image, the maximum of the irradiation time is predetermined from approximately 500 msec to approximately 2 seconds. Thus, the irradiation time is determined equal to or shorter than the maximum irradiation time.

The first radiation sensor 40 is in a shape of a rectangular parallelepiped, is as large as several centimeters, and detects a dose (instantaneous value) of X-rays emitted by the X-ray source 10. A detection result (or dose signal) from the first radiation sensor 40 is used for recognizing a start and end of irradiation of the X-rays. The first radiation sensor 40 is disposed in an end portion of a radiation field of the collimator 21, namely, a through space where X-rays travel directly to the imaging surface 65 of the FPD device 63 without passage through the body H. This is for the purpose of preventing the first radiation sensor 40 from lying in the area of the body H in the X-ray image to avoid failure in the proper imaging for diagnosis. It is possible to check the through space by turning on the halogen lamp 26 after positioning the body H suitably.

Figure 3:
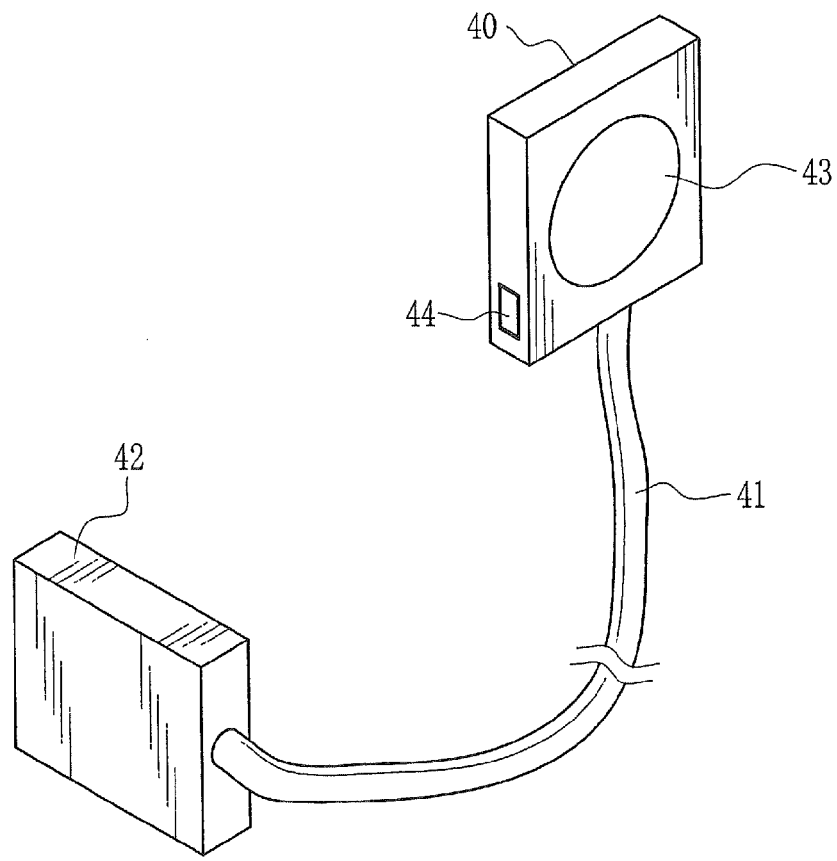
FIG. 3 is a perspective view illustrating the radiation sensor, a flexible support arm and a magnet.

In FIG. 3, a flexible support arm 41 (flexible support rod) of a bellows form with plural ring elements has an upper end to which the first radiation sensor 40 is attached. A direction and position of the first radiation sensor 40 can be changed in a range of extension of the flexible support arm 41. A magnet 42 as a fastening device is attached to a lower end of the flexible support arm 41. The magnet 42 attracts a wall of metal of the collimator 21 for fastening removably, for example, a sidewall. See FIG. 2.

A detection window 43 and a power switch 44 are disposed outside the first radiation sensor 40. The detection window 43 is constituted from a radio transparent plate for X-rays in the same manner as the radio transparent plate 25 of the collimator 21. The first radiation sensor 40 is so disposed as to oppose the detection window 43 to the radio transparent plate 25 of the collimator 21 directly. The power switch 44 is turned on manually by an operator before starting the X-ray imaging, and turned off after the termination of the imaging.

Figure 4:
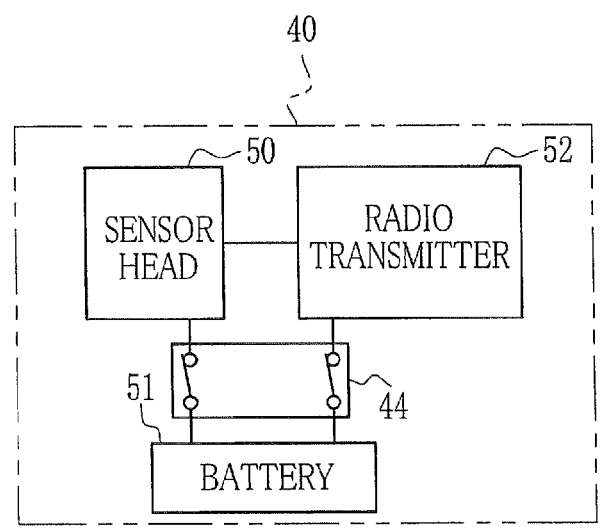
FIG. 4 is a block diagram schematically illustrating the radiation sensor.

In FIG. 4, the first radiation sensor 40 includes a sensor head 50, a battery 51 and a radio transmitter 52 or communication interface in a radio transmitter/receiver (subsystem). The sensor head 50 in the detection window 43 detects a dose of received X-rays through the detection window 43. The battery 51 supplies the sensor head 50 and the radio transmitter 52 with power when the power switch 44 is turned on. The radio transmitter 52 wirelessly transmits a detection result of the sensor head 50 at a predetermined interval of time as a dose signal, according to infrared communication of the IrDA standards, or the Wi-Fi (trade name) of the IEEE 802.11n standards at 2.4 GHz and 5.2 GHz.

Although there is a problem of crosstalk between the sensors disposed in two adjacent examination rooms, the Wi-Fi is useful because of reliability of the wireless communication on the condition of preventing crosstalk, for example, differences in frequency bands between the examination rooms. In relation to the infrared communication, there occurs a problem of an obstacle of blocking reception of an infrared output. However, this problem can be resolved easily by widening directivity of the infrared output or by removing the obstacle. The infrared communication is advantageous in the structural simplicity in the transmission unit, low power, low cost and easy handlability.

In FIG. 5, a communication interface 60 in the radio transmitter/receiver (subsystem) and a battery 61 are incorporated in the electronic cassette 13. The communication interface 60 communicates by a wired connection or wirelessly with the console unit 14 and the first radiation sensor 40. Signals transmitted by use of the communication interface 60 include a dose signal, image data and other information or signals in relation to an imaging control unit 62 for the FPD device. The battery 61 supplies the electronic cassette 13 with power for operating its various elements. The battery 61 is a comparatively small type and contained in the electronic cassette 13 with a small thickness. Also, the battery 61 can be charged in the outside of the electronic cassette 13 by a charger, for which a cradle is used to set the battery 61. Furthermore, a charging system of a wireless type can be used for charging the battery 61 wirelessly.

Failure may occur in the wireless communication between the electronic cassette 13 and the console unit 14 due to shortage in the remaining power of the battery 61. For such a situation, the communication interface 60 is connected to the console unit 14 by a wired connection. A cable is used between the communication interface 60 and the console unit 14 for the wired connection. Note that the electronic cassette 13 may be supplied with power by the console unit 14.

The FPD device 63 includes a TFT active matrix substrate with the imaging surface 65. A plurality of pixels 64 are arranged on the active matrix substrate for storing charge according to a dose of X-rays. The pixels 64 are arranged in plural arrays, or in a matrix form of n arrays (X direction) and m columns (Y direction) at a regular pitch.

The FPD device 63 has scintillator (phosphor) for converting X-rays to visible light, and is an indirect conversion type in which the visible light from the scintillator is photoelectrically converted by the pixels 64. The scintillator is formed from thallium-activated cesium iodide (CsI:Tl), and GOS or gadolinium oxysulfide ($Gd_2O_2S$:Tb). The scintillator is opposed fully to the imaging surface 65 where the pixels 64 are arranged. The FPD device 63 can be constructed by the PSS method (penetration side sampling method) in which the elements are arranged in an order of the scintillator and the active matrix substrate in the housing from the outer side of X-rays toward the inner side, or by the ISS method (irradiation side sampling method) in which its elements are arranged in an order of the active matrix substrate and the scintillator. Also, the FPD device 63 can be a direct conversion type in which a conversion layer of amorphous selenium and the like for directly converting X-rays into electric charge.

Each of the pixels 64 includes a photo diode 66, a capacitor (not shown) and a thin film transistor 67 (TFT). The photo diode 66 is a photoelectric conversion element for generating charge (electrons and positive holes) upon entry of visible light. The capacitor stores the charge generated by the photo diode 66.

The photo diode 66 has a structure including a semiconductor layer for generating charge, for example, of the PIN type, and upper and lower electrodes formed on the semiconductor layer. The thin film transistor 67 is connected to the lower electrode of the photo diode 66. A bias line is connected to the upper electrode. There are a plurality of such bias lines as many as n arrays of the pixels 64 on the imaging surface 65. Those are bundled in connection to a single signal line, which is connected to a bias power source. The bias power source applies bias voltage to the upper electrode of the photo diode 66 through the signal line and the bias lines. An electric field is created in the semiconductor layer by applying the bias voltage. Charge (electrons and positive holes) created in the semiconductor layer by the photoelectric conversion moves to the upper and lower electrodes having positive and negative polarities, so that a capacitor stores the charge.

The thin film transistors 67 have electrodes of a gate, source and drain. A scan line 68 is connected with the gate of the thin film transistors 67. A signal line 69 is connected with the source. Each of the photo diodes 66 is connected with the drain. The scan lines 68 and the signal lines 69 are disposed in a form of a grating. A number of the scan lines 68 is n or the array number of the pixels 64 on the imaging surface 65. A number of the signal lines 69 is m or the column number of the pixels 64. A gate driver 70 is connected with the scan line 68. A signal processing unit 71 is connected with the signal line 69.

The gate driver 70 drives the thin film transistors 67 for operation of storing, reading and resetting. In the storing, a signal charge according to the received dose of X-rays is stored in the pixels 64. In the reading, the signal charge is read from the pixels 64. The imaging control unit 62 controls time points of start of the storing, reading and resetting of the gate driver 70.

In the storing, the thin film transistors 67 are kept turned off, while the pixels 64 are caused to store the signal charge. In the reading, the gate driver 70 successively generates gate pulses G1-Gn for simultaneously driving the thin film transistors 67 of common arrays. The scan lines 68 are activated one after another, to turn on the thin film transistors 67 by one array in connection with the scan lines 68. The signal charge stored in the capacitor of the pixels 64 is read through the signal line 69 when the thin film transistors 67 are turned on, and is input to the signal processing unit 71.

The signal processing unit 71 includes amplifier integrators 72, CDS devices 73 (correlated double samplers), an MUX 74 (multiplexer) and an A/D converter 75. The amplifier integrators 72 are connected with the signal lines 69 discretely from one another. Each of the amplifier integrators 72 includes an operational amplifier 72a and a capacitor 72b connected between an input and output of the operational amplifier 72a. Each of the signal lines 69 is connected with a first one of the input terminals of the operational amplifier 72a. A second one of the input terminals of the operational amplifier 72a is grounded. A reset switch 72c is connected in parallel with the capacitor 72b. The amplifier integrators 72 store charge input by the signal lines 69, and convert the charge into analog voltage signals V1-Vm to output the voltage signals. The MUX 74 is connected to output terminals of the operational amplifiers 72a of the array by use of amplifiers 76 and the CDS devices 73. The A/D converter 75 is connected to an output terminal of the MUX 74.

A sample-hold circuit is incorporated in the CDS devices 73, and eliminates noise by correlation double sampling of the voltage signal output by the amplifier integrators 72. The sample-hold circuit holds the voltage signal of each of the amplifier integrators 72 for a predetermined time (sample-hold). The MUX 74 responds to a control signal from a shift register (not shown), and selects one of the CDS devices 73 from each one of their columns in parallel by use of an electronic switch. The voltage signals V1-Vm output by the selected CDS devices 73 are input to the A/D converter 75 serially. A memory 77 is incorporated in the electronic cassette 13. The A/D converter 75 converts the voltage signals V1-Vm to digital voltage signals, which are written to the memory 77. Note that an amplifier may be connected between the MUX 74 and the A/D converter 75.

When the MUX 74 reads the voltage signals V1-Vm of one array from the amplifier integrators 72, the imaging control unit 62 outputs a reset pulse RST to the amplifier integrators 72, so that the reset switch 72c is turned on. The signal charge of the one array, which is stored in the capacitor 72b, is discharged for resetting. After this, the reset switch 72c is turned off again, to hold one of the sample-hold circuits in the CDS devices 73 upon a lapse of a predetermined time. A kTC noise component of the amplifier integrators 72 is sampled. Then a gate pulse of a second array is output by the gate driver 70, to start reading signal charge of the pixels 64 of the second array. Upon a lapse of a predetermined time after outputting the gate pulse, the signal charge of the pixels 64 of the second array is held by a second one of the sample-hold circuits in the CDS devices 73. Those steps are successively repeated to read the signal charge of the pixels 64 of all the arrays.

When all the arrays are read completely, the memory 77 stores image data of the X-ray image of one frame. The image data is read from the memory 77, and output to the console unit 14 by use of the communication interface 60. Thus, the X-ray image of the body H is detected.

A dark current is generated in the semiconductor layer of the photo diodes 66 irrespective of entry of X-rays. The dark current is stored in the capacitor of the pixels 64 owing to application of the bias voltage. The dark current at the pixels 64 comes to constitute a noise component in the image data. Resetting is carried out at an interval of a predetermined time for eliminating the noise. In the resetting, the dark current generated at the pixels 64 is discharged through the signal lines 69.

An example of the method of the resetting is sequential resetting in which the pixels 64 are reset by one array. In a manner similar to reading of a signal charge, the gate driver 70 successively sends gate pulses G1-Gn to the scan lines 68, and turns on the thin film transistors 67 of the pixels 64 by one array. While each of the thin film transistors 67 is turned on, a dark current from the pixel 64 flows to the capacitor 72b of the amplifier integrator 72 through the signal line 69. As a difference of the resetting from the reading, no charge from the capacitor 72b is read by the MUX 74. The imaging control unit 62 outputs a reset pulse RST in synchronism with each of the gate pulses G1-Gn to turn on the reset switches 72c. The charge in the capacitors 72b is discharged to reset the amplifier integrators 72.

Instead of the sequential resetting, the region resetting and the total resetting can be used. In the region resetting, pixels are grouped in plural groups each of which is constituted by a predetermined number of arrays of pixels. Pixels of each of the groups are reset in the sequential resetting, to discharge dark current simultaneously from the arrays of the various groups. In the total resetting, agate pulse is input for all of the arrays to discharge dark current of all the pixels simultaneously. According to the region resetting and the total resetting, it is possible to quicken resetting operation.

Various circuits (not shown) for image processing are incorporated for X-ray image data from the memory 77 for such functions as offset correction, sensitivity correction and defect correction. The offset correction circuit subtracts an offset correction image from an X-ray image for each of pixels, and eliminates fixed pattern noise due to specificity or imaging environment of the signal processing unit 71, the offset correction image having been obtained from the FPD device 63 without irradiation of X-rays.

The sensitivity correction circuit is a gain correction device for correcting unevenness in sensitivity of the photo diodes 66 of the pixels 64 and unevenness of a characteristic of output of the signal processing unit 71. The sensitivity correction is carried out according to sensitivity correction data. Specifically, a test image is previously created by applying X-rays of a predetermined dose without presence of the body H. The offset correction image is subtracted from the test image to create the sensitivity correction data. The sensitivity correction data includes coefficients for respective pixels for correcting a difference from a reference value. When irradiation of X-rays of the predetermined dose without presence of the body H is carried out, the coefficients are multiplied by the X-ray image after the offset correction so as to regularize outputs of the pixels. For example, let an output of a pixel A be 1 as a reference value. An output of a pixel B is 0.8. Then a coefficient for the pixel B is 1/0.8=1.25.

The defect correction circuit corrects a pixel value of a defective pixel by linear interpolation of pixel values of peripheral normal pixels around the defective pixel and according to defective pixel information which has been added in the course of shipment.

The offset correction image and the sensitivity correction data are acquired at the time of shipment of the electronic cassette 13, at the time of periodical maintenance by a service technician of a manufacturer, or at the start of working hours of a hospital by a medical technician or operator. The offset correction image and the sensitivity correction data are written in an internal memory in the imaging control unit 62 and read at the time of correction. Also, the above-described circuits for the image processing of the various functions can be incorporated in the console unit 14, in which the image processing of the various functions can be carried out.

An evaluation unit 78 for detecting a start and end of the irradiation is controlled by the imaging control unit 62. The evaluation unit 78 reads the dose signal received by the communication interface 60 with the imaging control unit 62, and detects a start and end of the irradiation of X-rays according to the dose signal. Specifically, the dose signal is compared with thresholds for evaluation stored previously. The evaluation unit 78, when the dose signal becomes equal to or higher than a first threshold, detects a start of the irradiation, and when the dose signal becomes lower than a second threshold, detects an end of the irradiation.

The operation of imaging in the X-ray imaging system 2 is described now. At first, the body H (object) of the patient is made to stand at the floor stand 15 or lie on the examination table 16. A height or horizontal position of the electronic cassette 13 on either one of the floor stand 15 and the examination table 16 is adjusted and set for the position of the body H. A height or horizontal position of the X-ray source 10 and a size of a radiation field are adjusted according to the position of the electronic cassette 13 and the size of a body part of interest. Then the controllable power supply 11 and the console unit 14 are started up with information of an imaging condition.

Figure 6:
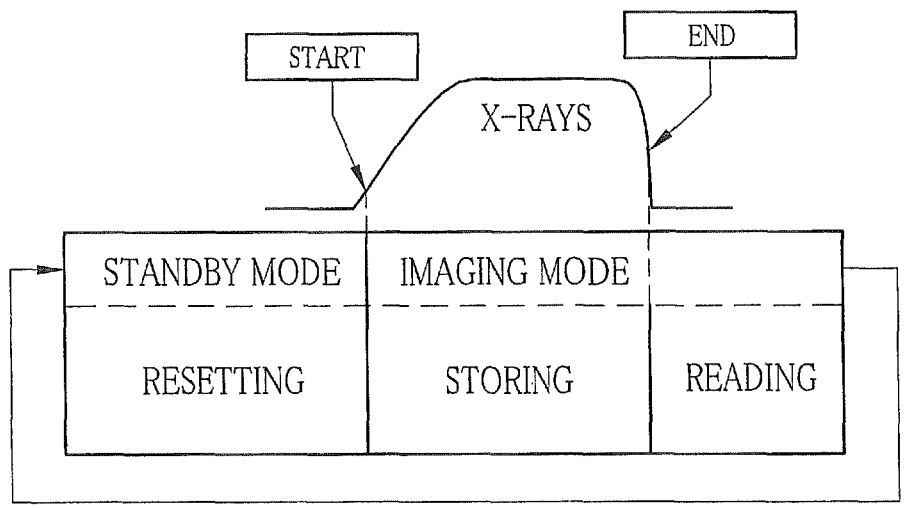
FIG. 6 is a timing chart illustrating operation of an FPD device in X-ray imaging.

In FIG. 6, a standby mode before imaging is illustrated. The imaging control unit 62 causes the FPD device 63 to operate for resetting repeatedly. When the radiation switch 12 is depressed in the two stages, the X-ray source 10 starts emitting X-rays. The evaluation unit 78 detects a start of irradiation of the X-rays by checking an increase of a dose signal to the threshold. Then the imaging control unit 62 causes the FPD device 63 to stop the resetting and to start the storing, and changes over the standby mode to the imaging mode. When the irradiation time according to the imaging condition elapses, irradiation of X-rays from the X-ray source 10 is stopped. The evaluation unit 78 detects an end of irradiation of the X-rays by checking a decrease of a dose signal down to the threshold. Then the imaging control unit 62 changes over the FPD device 63 from the storing to the reading. Thus, an image of one frame is finally created. After the reading, the FPD device 63 comes again to the standby mode.

The charge generated by application of X-rays from the X-ray source 10 is stored in the pixels 64 by the storing operation, and is output and written to the memory 77 as X-ray image data by the reading operation. The circuits for image processing in the imaging control unit 62 process the X-ray image data from the memory 77 in the image processing of various functions, so as to create an X-ray image of one frame. The communication interface 60 transmits the X-ray image to the console unit 14 by a wired connection or wirelessly. The display panel 14b is driven to display the X-ray image for diagnosis.

As has been described heretofore, the first radiation sensor 40 is disposed in the path of the irradiation of X-rays toward the body H in a changeable manner. The first radiation sensor 40 can be present on the side of the X-ray source 10 upstream of the body H, for example, near to the radio transparent plate 25 of the collimator 21 (aperture device).

X-rays are attenuated by passage through the body H. If a radiation sensor is disposed in a portion of the imaging surface 65 corresponding to an area of the body H, energy of the X-rays incident upon the radiation sensor is lower. A resolution of detection of the first radiation sensor 40 must be set high. Considerably long time is required for detecting a start and end of the irradiation. If the energy of X-rays in the imaging is so high that the attenuation caused by the body H is sufficiently small, there is no problem in the detection of the start and end. However, if a patient with the body H is a slender person or child, or if the energy of X-rays in the imaging is relatively low, then considerable time is required for detecting the start and end of the irradiation, or no result of the detection can be obtained successfully. In the present embodiment, the first radiation sensor 40 is disposed upstream of the body H on the side of the X-ray source 10. Thus, no high resolution for detection is required in the first radiation sensor 40. The start and end of the irradiation can be detected without delay even for imaging with low energy of X-rays.

Intensity of X-rays is inversely proportional to the square of the distance. A dose of X-rays incident upon the first radiation sensor 40 decreases according to an increase in the distance of the first radiation sensor 40 to the exit aperture of the X-rays. It is possible to eliminate influence of the attenuation of X-rays according to the distance by disposing the first radiation sensor 40 near to the exit aperture of the X-rays.

The FPD device 63 is changed over for storing charge immediately upon detecting the start of the irradiation. Thus, the X-rays can be fully utilized for creating X-ray images without waste. As a result, the end of the irradiation can be earlier. Dose of X-rays to the body H can be reduced effectively.

The first radiation sensor 40 and the magnet 42 are connected to respective ends of the flexible support arm 41, so that the first radiation sensor 40 is shiftable in a range determined by the length of the flexible support arm 41. Thus, degree of freedom of disposition of the first radiation sensor 40 can be higher than an attached structure of disposing the magnet 42 or other fastening device directly on the first radiation sensor 40. Also, the first radiation sensor 40 can be disposed in a through space with great ease smoothly.

Figure 7:
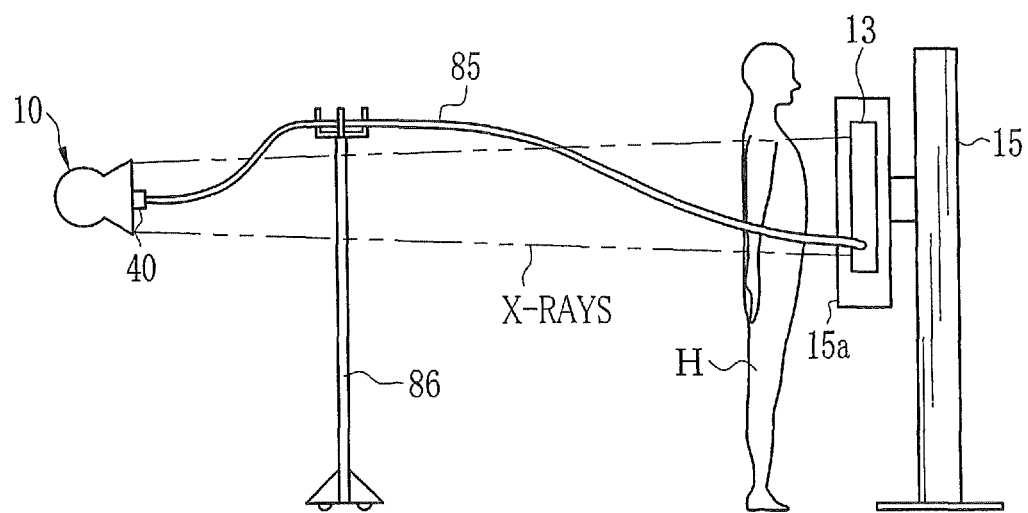
FIG. 7 is an explanatory view in elevation illustrating an example of connecting the radiation sensor to the electronic cassette by a wired connection.

In the above embodiment, the dose signal is wirelessly sent from the first radiation sensor 40 to the electronic cassette 13. In contrast, FIG. 7 illustrates a preferred embodiment in which a signal line 85 or cable is used between the electronic cassette 13 and the first radiation sensor 40. The dose signal is transmitted from the first radiation sensor 40 to the electronic cassette 13 by the signal line 85 of a wired connection. For such a structure, a ceiling mount may be disposed to suspend the X-ray source 10 from the ceiling of the examination room. Preferably, an infusion stand 86 is additionally used for locally supporting the signal line 85 between the high position of the X-ray source 10 and the electronic cassette 13.

Also, a fastening structure such as the magnet 42 may be formed together with the first radiation sensor 40 as one portion. The first radiation sensor 40 can be positioned on the rail 29 or the front guard 30 for setting an additional filter for the collimator 21.

It is possible inside the collimator 21 to dispose the first radiation sensor 40 in one of surplus spaces where X-rays always leak uselessly without determining the image. Examples of such surplus spaces are the inside of a coupling sleeve 31 or joint portion between the X-ray tube 20 and the collimator 21 and having the collimator plate 24*c*, and spaces 32 and 33 between the collimator plates 24*a*-24*c* of FIG. 2. For such a structure, a fastener is attached to the first radiation sensor 40 itself. A dose signal (dose information) is wirelessly transmitted from the first radiation sensor 40 to the electronic cassette 13. It is unnecessary to check whether the first radiation sensor 40 is disposed properly in the through space, and to check the radiation field. Also, the leakage can be effectively reduced, as the first radiation sensor 40 is disposed properly for the position of receiving leaked X-rays. Note that access to the relevant space in the collimator 21 should be facilitated. To this end, it is preferable to construct a housing of the collimator 21 in an easily disassemblable form by manual touch, or to dispose an openable lid for the relevant space. Visible information can be indicated to clarify the position of the first radiation sensor 40, for example, a marker, sticker, seal and the like with an indicia.

Also, the first radiation sensor 40 may be fastened to an outer surface of the housing of the collimator 21. The housing is constructed to shield X-rays from the inside of the collimator 21 so as to prevent radioactive exposure. However, the housing has portions where radiopaque parts of lead or the like are difficult to dispose for the structural reason. Among the parts, X-rays are very likely to leak at the coupling sleeve 31 and the spaces 32 and 33 between the collimator plates 24*a*-24*c*. It is possible to dispose the first radiation sensor 40 in at least one of those parts. The first radiation sensor 40 is effective in detecting leaked X-rays and in shielding X-rays to prevent unwanted exposure. Also, it is unnecessary to disassemble the housing of the collimator 21, which can have good operability and suitability for maintenance.

Figure 8:
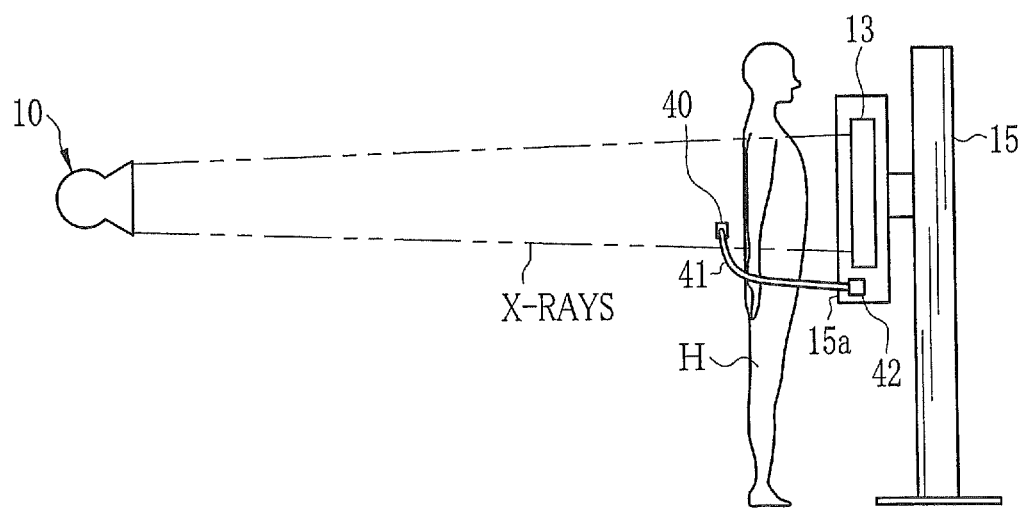
FIG. 8 is an explanatory view in elevation illustrating an example of the radiation sensor disposed behind a body.

Also, the first radiation sensor 40 can be disposed on the side of the body H instead of the vicinity of the radio transparent plate 25 of the collimator 21. In FIG. 8, the magnet 42 as a fastener is mounted on a side surface of the holder 15*a* of the floor stand 15. The flexible support arm 41 is extended suitably to position the first radiation sensor 40 in a through space upstream of the body H to oppose the detection window 43 to the radio transparent plate 25 exactly.

Also, a body fastener can be used, and coupled to the first radiation sensor 40 directly. The body fastener is set directly on the body H to position the first radiation sensor 40. For this structure, the first radiation sensor 40 is not disposed in the through space, but in an area which is distinct from a region of interest of the body H as an important target site in the examination. For example, a chest of the body H is imaged. The region of interest is areas of lungs on the right and left sides. Although X-rays may attenuate due to a long distance from the first radiation sensor 40 to the exit aperture for X-rays, attenuation according to this structure is as small as 1/10 of that in a structure where the first radiation sensor 40 is disposed in a portion of the imaging surface 65 corresponding to the body H.

Also, the first radiation sensor 40 can be fastened to a shoulder, arm or the like the body H to protrude outwards or laterally, and positioned in a through space in the radiation path of the X-rays.

Figure 9:
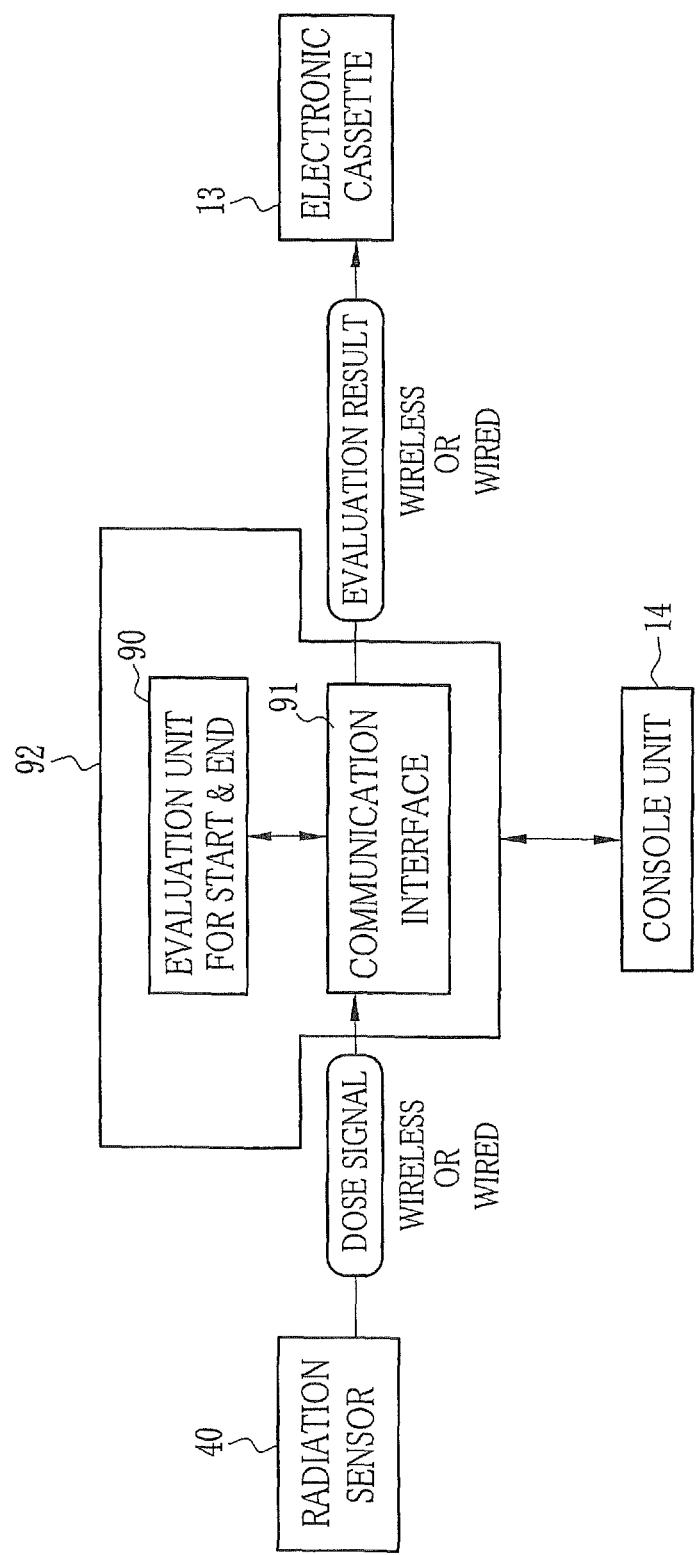
FIG. 9 is a block diagram schematically illustrating circuit elements in a cassette control unit.

In FIG. 9, a preferred embodiment is illustrated. A cassette control unit 92 or additional control unit for the electronic cassette 13 includes an evaluation unit 90 for detecting a start and end of the irradiation, and a communication interface 91. The evaluation unit 90 is structurally the same as the evaluation unit 78. The communication interface 91 receives the dose signal, and transmits an evaluation result from the evaluation unit 90. The cassette control unit 92 is placed between the electronic cassette 13 and the console unit 14, and sends and receives information of various kinds between the electronic cassette 13 and the console unit 14. The cassette control unit 92 is disposed near to the holder 15*a* of the floor stand 15 or the holder 16*a* of the examination table 16, or incorporated in one of the holders 15*a* and 16*a*. Transmission of the dose signal from the first radiation sensor 40 to the communication interface 91 and transmission of the output of the evaluation unit 78 from the communication interface 91 to the electronic cassette 13 can be carried out by a wired connection or wirelessly.

Figure 10A:
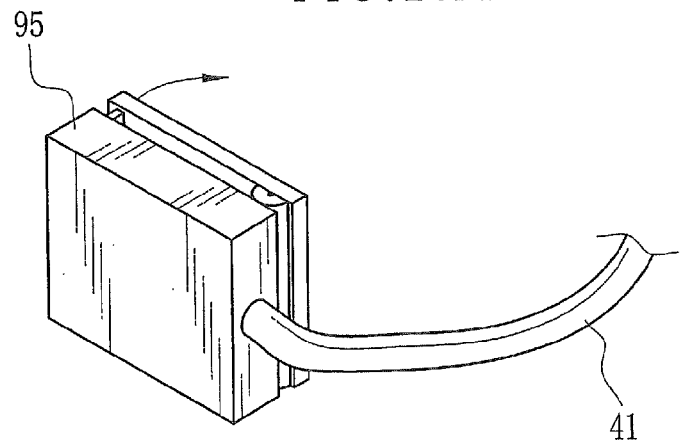
FIG. 10A is a perspective view illustrating a clip as another preferred fastening device.
Figure 10B:
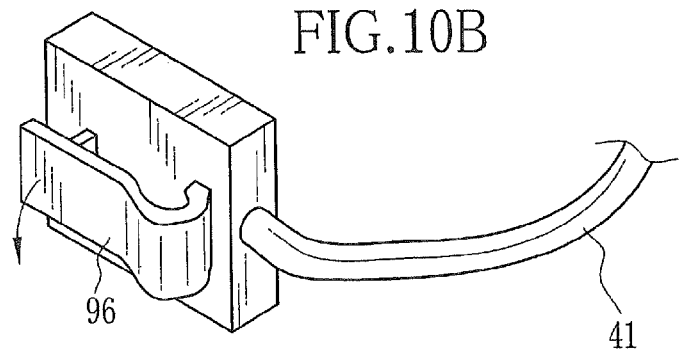
FIG. 10B is a perspective view illustrating another preferred clip with a plate spring.
Figure 10C:
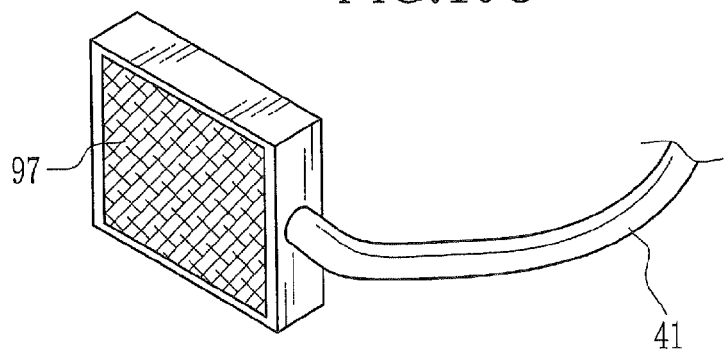
FIG. 10C is a perspective view illustrating a touch fastener as still another preferred fastening device.

Furthermore, fastening devices other than the magnet 42 can be used. To fasten the first radiation sensor 40 directly to the body H, a fastening device different from the magnet 42 is required. Specifically, FIG. 10A illustrates a clip device 95 with a hinge as a fastening device. In FIG. 10B, a clip device 96 with a plate spring is illustrated. In FIG. 10C, a touch fastener 97 or Velcro fastener as a fastening device is illustrated. A selected one of a hook pad of many hooks and a loop pad of many loops is included in the touch fastener 97. A second one of the hook pad and loop pad is attached to a target surface of the body H for fastening of the touch fastener 97. Also, an adhesive tape can be used for fastening. Various known fastening devices can be also used. In the drawings, the flexible support arm 41 is combined with any one of the fastening devices. However, a fastening device can be directly associated with the first radiation sensor 40 itself.

Figure 11:
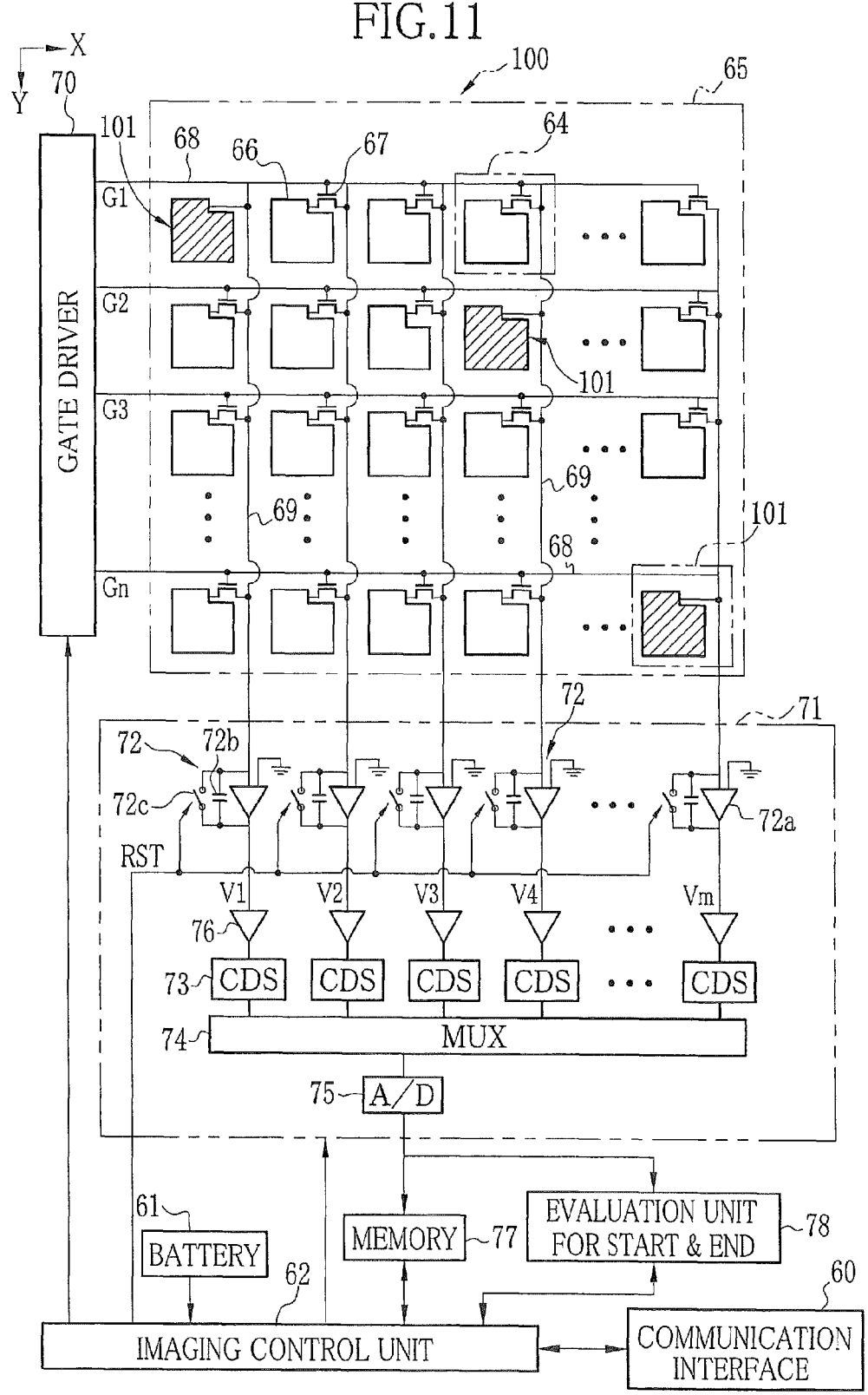
FIG. 11 is a block diagram schematically illustrating the FPD device with a radiation sensor on an imaging surface.

In FIG. 11, another preferred embodiment is illustrated. An FPD device 100 (flat panel detector device) or detector panel has a part of the pixels 64 for use as a radiation sensor, which operates on the imaging surface 65 in a discrete manner from the first radiation sensor 40.

On the imaging surface 65 of the FPD device 100 are arranged a plurality of detection pixels 101 as a second radiation sensor or dosimeter. Although the pixels 64 are connected by the thin film transistors 67 to the signal lines 69, the detection pixels 101 are connected to the signal lines. 69 without the thin film transistors 67. The detection pixels 101 are used for detecting a dose of X-rays to the imaging surface 65. A ratio of the detection pixels 101 to the pixels 64 on the imaging surface 65 is from several ppm (parts per million) to several percent.

The detection pixels 101 are disposed regularly on the whole of the imaging surface 65 without local unevenness. One of the detection pixels 101 is included in one pixel column of pixels to which the signal line 69 is commonly connected. One of the numerous pixel columns, which includes one of the detection pixels 101, is regularly arranged in a manner alternate with two or three adjacent pixel columns without the detection pixels 101. Positions of the detection pixels 101 are predetermined at the time of manufacturing the FPD device 100. Information of the positions (coordinates) of all the detection pixels 101 is stored in a non-volatile memory (not shown) in the FPD device 100. Note that positions of the detection pixels 101 may be modified as desired, for example, can be near to one another in a locally collected manner. Specifically, the detection pixels 101 for use in a mammography system can be disposed commonly for a thoracic wall of the body H.

As no thin film transistor is provided between the detection pixels 101 and the signal lines 69, a signal charge generated by the detection pixels 101 is transmitted directly through the signal lines 69. This is the situation even while the thin film transistors 67 at the pixels 64 are turned off for the storing operation to store the charge. Thus, the charge from each of the detection pixels 101 always flows to the capacitor 72b of the amplifier integrator 72 on the signal line 69 in connection with the detection pixel 101. In the storing operation, the charge stored in the capacitor 72b after generation in the detection pixel 101 is read from the amplifier integrator 72 at a predetermined sampling period, converted into a digital voltage signal by the A/D converter 75, and output to the evaluation unit 78. To detect a start of the irradiation, the FPD device 100 is changed over from the resetting to the storing when the imaging condition is set in the console unit 14. At the same time, sampling of the voltage signal according to the charge generated by the detection pixels 101 is started.

The evaluation unit 78 detects the start and end of irradiation not only according to the dose signal from the first radiation sensor 40, but also according to a voltage signal based on the charge generated by the detection pixels 101. The evaluation unit 78 operates by comparison of the voltage signal and the threshold in the same manner as the detection from the dose signal.

The evaluation unit 78 reads a voltage signal from the detection pixels 101 in a through space for use in detecting a start and end of irradiation. In the through space, a dose of X-rays is higher on the imaging surface 65 than in an area of the body H. A change amount of the dose per unit time is also higher. It is possible in a short time to obtain a voltage signal with a sufficient value of the S/N ratio for detecting a start and end of the irradiation. The evaluation can be carried out quickly and exactly.

The through space can be determined by manual operation for inputting of an operator, or according to monitoring a voltage signal. Also, the voltage signal expressing a maximum value can be used for detecting a start and end of the irradiation. For this operation, the through space is not determined. Thus, it is possible to shorten the time for the detection effectively.

In short, the use of the detection pixels 101 discrete from the first radiation sensor 40 makes it possible to change over the modes. For imaging with a low dose, the dose signal from the first radiation sensor 40 is utilized to detect a start and end of the irradiation. For imaging with a high dose, the voltage signal according to the charge from the detection pixels 101 is utilized. Note that the changeover between the first radiation sensor 40 and the detection pixels 101 can be made by manual operation of the input interface 14a, or by automatic control of the imaging control unit 62 according to the input imaging condition.

Also, the first radiation sensor 40 may be used for detecting the start and end of the irradiation. The detection pixels 101 may be used as a radiation sensor of the AEC (or automatic exposure control). Furthermore, plural detection modes of changeover can be predetermined for the use of the first radiation sensor 40 and the detection pixels 101. If communication from the electronic cassette 13 to the controllable power supply 11 is impossible as described in the above embodiments, a first detection mode can be set to use the first radiation sensor 40. If a communication interface is incorporated in the controllable power supply 11 and is on-line with the electronic cassette 13, a second detection mode can be set to use the detection pixels 101.

In case of using the detection pixels 101 for the AEC, signal values are accumulated in relation to the voltage signal according to charge of one of the detection pixels 101 corresponding to the most important region of interest for the examination within the whole region of the body H, the signal values including a sum, average, maximum and mode value of the voltage signal. Such an accumulated value is compared with the predetermined threshold for the stop. If the accumulated value becomes equal to or more than the threshold, it is judged that the accumulated dose of X-rays to the region of interest has come up to the reference dose. Then a control signal for stop is input to the controllable power supply 11. In response, the controller 36 of the controllable power supply 11 stops supply of power from the high voltage source 35 to the X-ray tube 20. The irradiation of X-rays is stopped.

Note that the first radiation sensor 40 and the detection pixels 101 are not used simultaneously or are not switched to one another in the course of imaging. It is preferable in the communication interface 60 to use one interface device commonly for receiving the dose signal and transmitting a stop signal for the irradiation, a sync signal and the like. This is because the use of the single interface device is less costly than the use of plural interface devices for plural purposes.

In the above embodiment, the detection pixels 101 constitute the second radiation sensor connected directly to the signal line 69. Furthermore, other detection of radiation may be used. For example, a TFT is connected to each of special detection pixels, and driven by a gate driver and scan line which are different from those for the pixels 64. The detection pixels store charge to be read in a discrete manner from the pixels 64. Furthermore, a control of monitoring a current can be used. A radiation dose is detected by monitoring a current on a bias line connected to a particular one of pixels. This is on the basis of a flow of a current on the bias line for supply of bias voltage to the pixel according to the charge generated by the pixel. If all of the TFTs are turned off, a dose can be detected according to charge leaked from the pixels.

In the above embodiments, the electronic cassette 13 is a component separate from the console unit 14. However, the console unit 14 may not be separate. A section of the electronic cassette 13 can be incorporated in the console unit 14. The radiation detector in the above embodiments is the electronic cassette 13 of a portable form, but can be a large type for stationary installation in the examination room.

Figure 12:
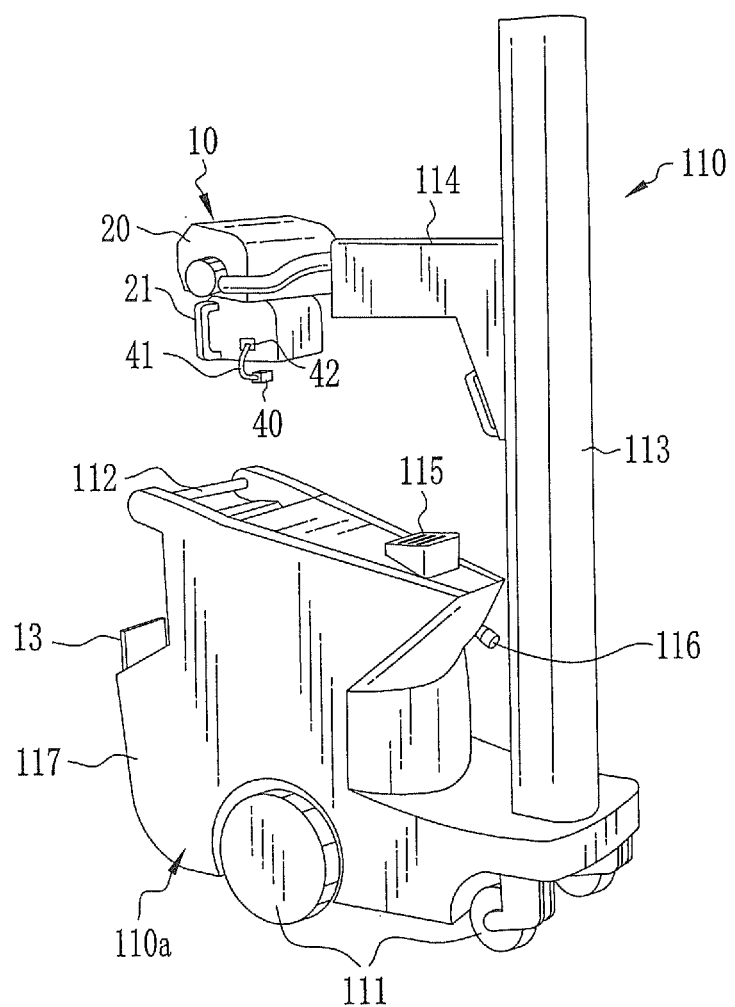
FIG. 12 is a perspective view illustrating an X-ray imaging system of a bedside type.

In FIG. 12, another preferred embodiment of X-ray imaging system 110 of a bedside type or a medical cart is illustrated. The X-ray imaging system 110 is mobile in a corridor or patient's room for bedside examination. A mobile cart housing 110a has cart wheels 111 and a cart handle 112. The X-ray imaging system 110 includes a support post 113 and an arm 114. The support post 113 is rotatable around its axis. The arm 114 supports the X-ray source 10 at its tip, and is mounted on the support post 113 movably up and down. The X-ray source 10 can be positioned as desired by the operator. A battery charger 115 and a power supply plug 116 of a power cable are disposed nearer to the support post 113 than the cart handle 112. The battery charger 115 charges the battery 61 in the electronic cassette 13. The power supply plug 116 is supplied with external power. A pocket 117 is disposed under the cart handle 112 for containing the electronic cassette 13. A touch panel (not shown) is disposed on the cart housing 110a, and operable for inputting an imaging condition and displaying X-ray images. Also, the cassette control unit 92 is contained in the cart housing 110a.

In the embodiment, the magnet 42 is placed on a lateral surface of the collimator 21 in a manner similar to FIG. 2, to position the first radiation sensor 40 of the wireless connection near to the radio transparent plate 25 by use of the flexible support arm 41. In use of the first radiation sensor 40 of the wired type illustrated in FIG. 7, the signal line 85 can be extended along the support post 113 and the arm 114 and positioned by use of a bundling band, wiremold and the like. In the X-ray imaging system 110, power of the X-ray source 10 is lower than that in the X-ray imaging system 2 installed in the examination room in a stationary manner. Dose of the radiation is lower. Accordingly, remarkable effect can be obtained in the X-ray imaging system 110 in the present invention.

The radiation for imaging is X-rays according to the above embodiment, but can be gamma rays or the like according to the present invention.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging apparatus comprising:
   a radiation detector, having a detector panel, for receiving radiation applied by a radiation source to an object, and storing charge according to a radiation dose of said radiation, to create an image;
   a first radiation sensor for detecting said radiation dose;
   an evaluation unit for recognizing at least one of a start and an end of application of said radiation according to a dose signal from said first radiation sensor;
   a control unit for controlling said detector panel according to an evaluation result of said evaluation unit;
   a flexible support arm having a first end to which said first radiation sensor is attached; and
   a fastening device attached to a second end of said flexible support arm, said second end being different from said first end of said flexible support arm,
   wherein said first radiation sensor is secured removably in a radiation path between said radiation source and said object by said fastening device, and said first radiation sensor is kept in a changeable position in a range of the length of said flexible support arm.

2. The radiation imaging apparatus as defined in claim 1, wherein said fastening device includes a magnet device.

3. The radiation imaging apparatus as defined in claim 1, wherein said fastening device includes a clip device.

4. The radiation imaging apparatus as defined in claim 1, wherein said fastening device is formed together with said first radiation sensor.

5. The radiation imaging apparatus as defined in claim 1, wherein said dose signal is transmitted wirelessly from said first radiation sensor to said evaluation unit.

6. The radiation imaging apparatus as defined in claim 1, wherein said dose signal is transmitted by a signal line from said first radiation sensor to said evaluation unit.

7. The radiation imaging apparatus as defined in claim 1, wherein said first radiation sensor is disposed near to an exit aperture of said radiation source for emitting said radiation.

8. The radiation imaging apparatus as defined in claim 1, wherein said first radiation sensor is disposed in an area where said radiation leaks from said radiation path at said radiation source.

9. The radiation imaging apparatus as defined in claim 1, wherein said support arm extends toward said radiation source from a side of said radiation detector opposed to said object, and allows said first radiation sensor at an arm end thereof to enter said radiation path between said radiation source and said object.

10. The radiation imaging apparatus as defined in claim 1, wherein said control unit and said evaluation unit are incorporated in said radiation detector.

11. The radiation imaging apparatus as defined in claim 1, wherein said evaluation unit is external to said radiation detector, and transmits said evaluation result wirelessly or by a wired connection.

12. The radiation imaging apparatus as defined in claim 1, further comprising a second radiation sensor, disposed on said detector panel, for detecting said radiation dose discretely from said first radiation sensor.

13. The radiation imaging apparatus as defined in claim 12, wherein said second radiation sensor is used for automatic exposure control.

14. The radiation imaging apparatus as defined in claim 12, wherein said second radiation sensor is part of said pixels of said detector panel.

15. The radiation imaging apparatus as defined in claim 1, further comprising a communication interface, connected with said evaluation unit, for receiving said dose signal from said first radiation sensor, and transmitting said evaluation result to said control unit.

16. The radiation imaging apparatus as defined in claim 1, wherein said radiation detector includes a portable housing for containing said detector panel.

17. A radiation imaging apparatus comprising:
    a radiation detector, having a detector panel, for receiving radiation applied by a radiation source to an object, and storing charge according to a radiation dose of said radiation, to create an image;
    a first radiation sensor for detecting said radiation dose;
    an evaluation unit for recognizing a start and/or an end of application of said radiation according to a dose signal from said first radiation sensor;
    a control unit for controlling said detector panel according to an evaluation result of said evaluation unit;
    a fastening device for securing said first radiation sensor removably in a radiation path between said radiation source and said object; and
    a second radiation sensor, disposed on said detector panel, for detecting said radiation dose discretely from said first radiation sensor,
    wherein said control unit compares said radiation dose with a reference dose conditioned previously, and selects one of outputs of said first and second radiation sensors for use according to a result of comparison of said radiation dose.

18. A radiation imaging system comprising:
    a radiation source for applying radiation to an object;
    a radiation detector, having a detector panel, for receiving said radiation applied to said object, and storing charge according to a radiation dose of said radiation, to create an image;
    a first radiation sensor for detecting said radiation dose;
    an evaluation unit for recognizing at least one of a start and an end of application of said radiation according to a dose signal from said first radiation sensor;
    a control unit for controlling said detector panel according to an evaluation result of said evaluation unit;
    a flexible support arm having a first end to which said first radiation sensor is attached; and
    a fastening device attached to a second end of said flexible support arm, said second end being different from said first end of said flexible support arm,
    wherein said first radiation sensor is secured removably in a radiation path between said radiation source and said object by said fastening device, and said first radiation sensor is kept in a changeable position in a range of the length of said flexible support arm.

19. The radiation imaging system as defined in claim 18, further comprising a mobile housing for containing at least said radiation source, said mobile housing being mobile for a bedside use.

20. The radiation imaging system as defined in claim 18, wherein said flexible support arm extends toward said radiation source from a side of said radiation detector opposed to said object, and allows said first radiation sensor at an arm end thereof to enter said radiation path between said radiation source and said object.

* * * * *